United States Patent [19]

Norton

[11] 4,092,230

[45] May 30, 1978

[54] ELECTROCHEMICAL PROCESS FOR THE MANUFACTURE OF TEREPHTHALIC ACID

[75] Inventor: Richard V. Norton, Wilmington, Del.

[73] Assignee: Suntech, Inc., Wayne, Pa.

[21] Appl. No.: 776,454

[22] Filed: Mar. 10, 1977

[51] Int. Cl.$^2$ .................. C25B 3/00; C07C 51/08; C07C 63/26; C07C 63/28
[52] U.S. Cl. .................. 204/180 P; 204/72; 204/78; 260/515 P
[58] Field of Search ............ 204/72 US, 72, 78, 59 R, 204/180 P; 260/515 P

[56] References Cited

U.S. PATENT DOCUMENTS

| | | | |
|---|---|---|---|
| 2,770,588 | 11/1956 | Okada et al. | 204/72 |
| 3,086,928 | 4/1963 | Schultz | 204/72 |
| 3,113,964 | 12/1963 | Farkas et al. | 260/515 P |
| 3,393,220 | 7/1968 | Winnick et al. | 260/515 P X |
| 3,411,998 | 11/1968 | Wallman et al. | 204/98 |
| 3,781,343 | 12/1973 | Norton | 260/515 P |
| 3,849,243 | 11/1974 | Grot | 204/296 X |
| 3,968,017 | 7/1976 | Canata et al. | 204/180 P |

FOREIGN PATENT DOCUMENTS 756,854   9/1956   United Kingdom .................. 204/72

OTHER PUBLICATIONS

Basic Principles Organic Chemistry by Roberts et al., p. 558, pub. by Benjamin, New York, 1965.

Primary Examiner—F.C. Edmundson
Attorney, Agent, or Firm—J. Edward Hess; Donald R. Johnson; Paul Lipsitz

[57] ABSTRACT

A process for making terephthalic acid which comprises electrolyzing an aqueous solution of potassium acid terephthalate, preferably in the presence of a potassium salt of an acid stronger than terephthalic acid. In another embodiment of the invention terephthalonitrile is converted to terephthalic acid by hydrolyzing terephthalonitrile in an aqueous medium containing dipotassium terephthalate, potassium bicarbonate, and potassium hydroxide, stripping ammonia and carbon dioxide from the hydrolyzed product, adding carbon dioxide to the stripped hydrolysis product to precipitate monopotassium terephthalate, and electrolyzing said monopotassium terephthalate in the presence of an acid stronger than terephthalic acid to precipitate terephthalic acid and separating said terephthalic acid product.

7 Claims, 1 Drawing Figure

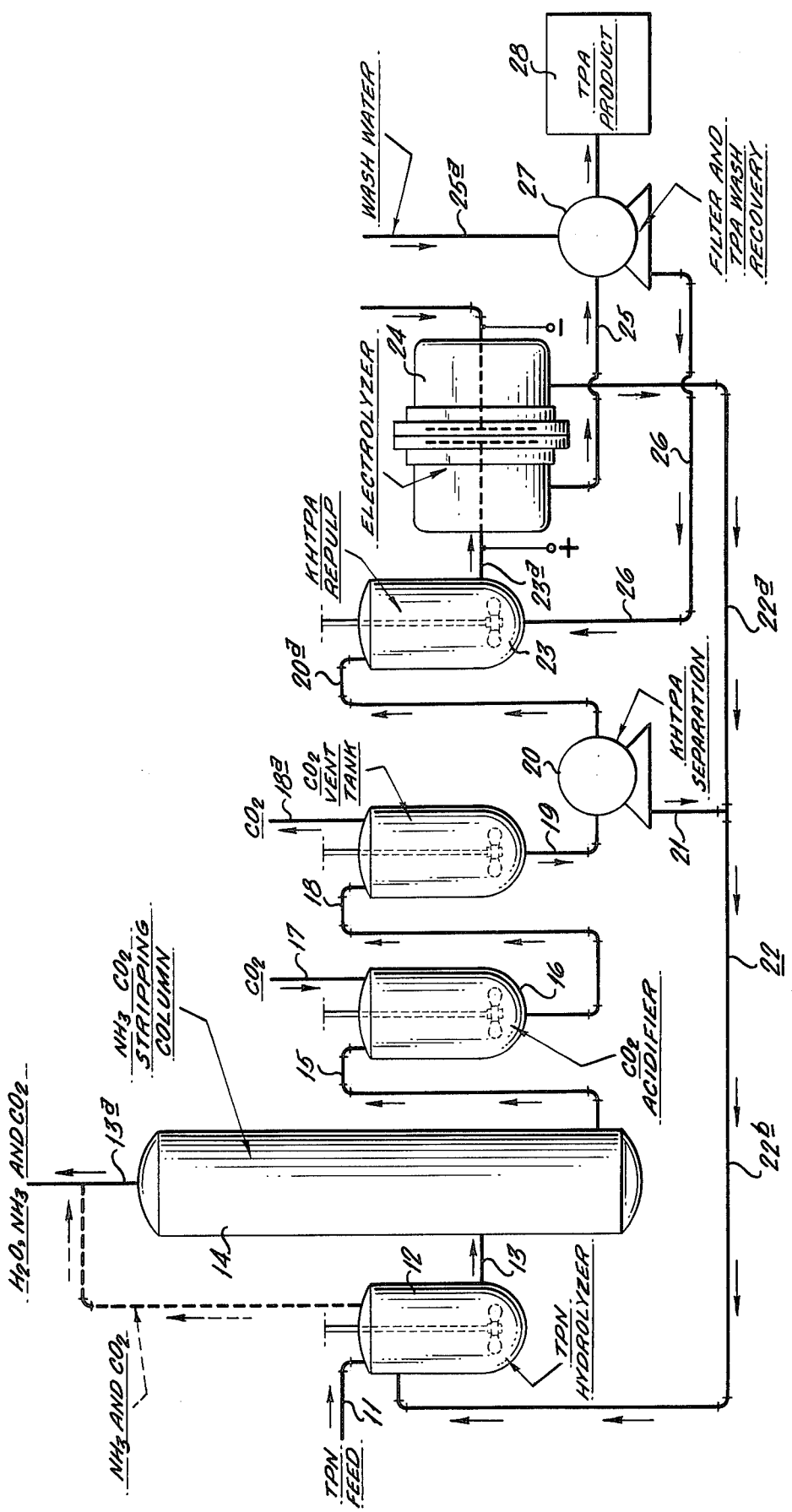

ELECTROCHEMICAL PROCESS FOR THE MANUFACTURE OF TEREPHTHALIC ACID

It is known in the art to hydrolyze terephthalonitrile in aqueous solution with or without catalysts to obtain terephthalic acid. In non-catalytic hydrolysis systems equilibrium reactions occur which cause nitrogen-containing intermediates to contaminate the terephthalic acid product. It therefore becomes extremely difficult to obtain the high purity terephthalic acid product needed for use as a polymer intermediate. Where alkaline catalysts (e.g. NaOH) are used for the nitrile hydrolysis, the product obtained will be an aqueous solution of the disodium salt of terephthalic acid and isolation of the free acid in pure form from such a solution is also difficult and expensive.

It is also known in the art to convert alkali metal carboxylic acid salts to free acid by electrolysis. More specifically, an alkali citrate is subjected to electrolysis to give the free acid (see for example U.S. Pat. No. 3,086,928 and 3,968,017). However, if pure citric acid is desired, then the alkali metal dihydrogen citrate is the starting material (U.S. Pat. No. 3,086,928). Where a di or tri-alkali metal salt is electrodialyzed as in U.S. Pat. No. 3,968,017 the product of the electrolysis is a mixture of salts and to obtain pure acid requires additional techniques to separate the unwanted salts.

It has now been found, unexpectedly, that free terephthalic acid (TPA) of relatively high purity can be obtained by electrolysis of the mono-potassium salt of terephthalic acid (i.e. potassium acid terephthalate, KHTPA), preferably in the presence of a potassium salt of an acid stronger than terephthalic acid.

In another embodiment of the invention terephthalonitrile is converted to terephthalic acid by hydrolyzing terephthalonitrile in an aqueous medium containing dipotassium terephthalate, potassium bicarbonate, and potassium hydroxide, stripping ammonia and carbon dioxide from the hydrolyzed product, adding carbon dioxide to the stripped hydrolysis product to precipitate monopotassium terephthalate, and electrolyzing said monopotassium terephthalate in the presence of an acid stronger than terephthalic acid to precipitate terephthalic acid and separating said terephthalic acid product.

In order to further illustrate and describe the process of the invention reference is made to the drawing which is an overall view of the process wherein terephthalonitrile is hydrolyzed and the mono-potassium salt of terephthalic acid electrolyzed.

It is seen that terephthalonitrile (TPN) is fed through line 11 to the hydrolyzer section 12 where hydrolysis occurs in the presence of $K_2TPA$, KOH and $KHCO_3$ which is introduced to the hydrolyzer by recycle from electrolysis cell 24 and separator 21 through line 22. Optionally, as shown by the dashed line, some ammonia and $CO_2$ may be removed from the hydrolyzer to shift the hydrolysis equilibria to the dipotassium salts. The hydrolyzate solution is passed by line 13 to a stripping column 14 where water, ammonia and $CO_2$ vapors are removed through line 13a. This stripping column 14 is generally operated at a molar ratio of ammonia to carbon dioxide of about 2:1 at which ratio the separation of the $CO_2$ and $NH_3$ from the aqueous solution is facilitated. The resulting aqueous solution from the stripping section 14 which is essentially an aqueous solution of $K_2TPA$ (ammonia content is generally less than 10 ppm) is taken through line 15 to a $CO_2$ acidifier 16 where $CO_2$ is introduced at line 17, preferably as a gas with good mixing to saturate the $K_2TPA$ solution at room temperature with carbon dioxide, the pH of the $CO_2$ treated solution becoming pH 7 or less. In this way an equilibrium is established resulting in precipitation of potassium hydrogen terephthalate (KHTPA). About 33 mole percent of the $K_2TPA$ is converted to KHTPA in this manner and an aqueous slurry is formed. It is significant to note that only the potassium salt is operative in this process, in spite of the disclosure of British Pat. No. 810,552 where Example 5 shows NaHTPA precipitating from a cold, $CO_2$ treated saturated solution of $Na_2TPA$. It may be that a very low temperature is needed for NaHTPA precipitation, but in a commercial process room temperature $CO_2$ saturation will be used and only the $K_2TPA$ salt is operative under such conditions. The slurry of KHTPA is taken by line 18 to a $CO_2$ vent tank where $CO_2$ gas is removed and then taken by line 19 to a separator 20 where the solids are separated and washed free of the filtrate containing $K_2TPA$, $KHCO_3$, $K_2CO_3$ and, a small amount of dissolved KHTPA. The mother and wash liquors are recycled to the hydrolysis reactor through lines 21, and 22b.

The damp crystalline KHTPA which is taken through line 20a is slurried in fresh water in a repulper 23 so as to obtain an aqueous slurry of the KHTPA at a concentration of from about 0.2 to about 1.0 molar, preferably from about 0.25 to 0.5 molar. A recycle stream 26 containing potassium salts of TPA and potassium salt by-products is recycled to repulper 23. The KHTPA suspension is then pumped through line 23a to the anode compartment of an electrolysis cell 24. A quantity of a potassium salt of an acid stronger in $pK_a$ than TPA is present in the electrolysis cell and this salt maintains high solution conductivity and ensures that the KHTPA can be completely converted to TPA without incurring a large ohmic resistance in the cell. In starting up the cell the potassium salt of the acid stronger in $pK_a$ than TPA (i.e. greater than a pKa of 4.8) is introduced as a onetime charge to the repulping tank and is then fed into the cell through line 23a and recycles to the cell through line 26. Occassionally a small amount of make-up salt is added to make up losses due to occlusion on the TPA product. The amount of this potassium salt of strong acid will be at least one mole, but preferably two to three moles per mole of KHTPA in the anolyte. Salts that can be used in this novel process are $K_2SO_4$, dipotassium hydrogen citrate, tripotassium citrate, potassium acetate, and the like. Application of an electric potential across the anode and cathode causes the potassium ions to migrate through the ion selective membrane and the following half reactions occur in each cell compartment.

ANODE

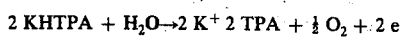

MEMBRANE

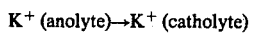

CATHODE

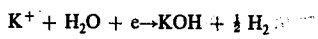

The terephthalic acid product is removed as a fine slurry from the anolyte compartment through line 25 to a suitable continuous filter 27 and the filtered material washed with water 25a after which it is separated as TPA product 28. Control of the KHTPA concentration relative to the potassium salt as well as control of the fluid flow rate through the cell is desirable in order to obtain complete conversion of KHTPA to TPA. It is also helpful to use a continuous pH control unit on the effluent anolyte slurry to maintain an optimum pH of about 3 to about 4 since a more basic pH of the effluent will result in incomplete conversion of KHTPA to TPA.

about 12 volts, about 5 to about 6.5 v. being preferred. The anode used will preferably be an electroplatinized inert metal such as columbium or titanium. The cathode material may be stainless steel.

The process of the invention is further illustrated by the flowsheet appearing as Table I which indicates the material balance in pound-moles per unit of time for the process shown in the FIGURE and described above. In carrying out the electrolysis the cell was operated at a current density of 280 ASF at 5.2 volts and the concentration of KHTPA in the cell anode compartment of the cell was 0.4 molar. The stream numbers correspond to the line numbers shown in the FIGURE.

TABLE 1

PROCESS STREAMS FOR TEREPHTHALIC ACID PROCESS OF DRAWING
(lb. moles per unit time)

| Stream No. | 11 | 13 | 13a | 15 | 17 | 18 | 18a | 19 | 20 |
|---|---|---|---|---|---|---|---|---|---|
| TPS | 1.00 | | | | | | | | |
| $K_2TPA$ | | 2.90 | | 2.90 | | 1.90 | | 1.90 | |
| KHTPA | | | | 1.00 | | 1.00 | | | |
| TPA | | | | | | | | | |
| $NH_3$ | | 2.00 | 2.00 | | | | | | |
| KOH | | | | | | | | | |
| $KHCO_3$ | | | | 1.00 | | 1.00 | | | |
| $CO_2$ | | 1.00 | 1.00 | | Sat'd | Sat'd | atm. press | | |
| $K_2SO_4$ | | | | | | | | | |
| $H_2O$ | | 447. | 92.4 | 354. | | 354. | | 354. | 85.0 |
| Temp. °C | | 150° | 80° | 100° | 30° | | | 30° | 30° |

| Stream No. | 20a | 23a | 25 | 25a | 28 | 24 | 26 | 22a | 21 | 22a |
|---|---|---|---|---|---|---|---|---|---|---|
| TPS | | | | | | | | | | |
| $K_2TPA$ | | | | | | | | | 1.90 | 1.90 |
| KHTPA | 1.00 | 1.00 | | | | | | | | |
| TPA | | | 1.00 | | 1.00 | | | | | |
| $NH_3$ | | | | | | | | | | |
| KOH | | | | | | | | 1.00 | | 1.00 |
| $KHCO_3$ | | | | | | | | | 1.00 | 1.00 |
| $CO_2$ | | | | | | | | | | |
| $K_2SO_4$ | | 2.83 | | | | | 2.83 | | | |
| $H_2O$ | 1.72 | 157.2 | 152. | 6.77 | 3.4 | 8.00 | 156. | 13.0 | 437. | 450. |
| Temp. °C | 30° | 80–90° | 90° | 90° | 90° | 90° | 90° | 90° | 30° | 30° |

The electrolytic cell used in the process will have a cation selective membrane separating the anode and cathode compartments. Such cells are known and the membrane will be a cation selective to the passage of metal ions (e.g. $Na^+$), but not anions (e.g. $OH^-$). A preferred membrane is a perfluorsulfonic acid resin which is exemplified by the free sulfonic acid form of a perfluorocarbon sulfonyl fluoride copolymer; e.g., a copolymer of a perfluorinated alpha olefin (e.g. TFE) with a sulfonyl fluoride perfluoro vinyl ether. These copolymers and their membranes are known as NAFION ® membranes are made by E. I. duPont de Nemours and Co., Inc., and are the subject of U.S. Pat. No. 3,282,875 which is hereby incorporated by reference.

Reference is also made to the DuPont magazine "Innovation" Volume 4, No. 3, Spring 1973 which discusses at pages 11 and 12 the chemistry of NAFION ® membranes and their use in electrolytic cells for plating and chlorine production. Similar perfluorocarboxylic acid membranes which are also useful in the process of this invention are disclosed by Maomi Seko in an article appearing in Ind. Eng. Chem., Prod. Res. Dev. Vol 15, No. 4, 1976, pages 286–292.

The electrolysis process will be operated at temperatures from about room temperature (e.g. about 20° C) to about 120° C. Preferred temperatures will be from about 90° C to about 110° C. Below 90° C, current density is lower than desirable, while above about 110° C, pressure develops in the cell system. Operating current density will be from about 100 to about 500 amps per square foot (ASF) at a voltage of from about 5 to

The invention claimed is:

1. A process for the preparation of terephthalic acid which comprises electrolyzing in the anode compartment of an electrolysis cell wherein said anode compartment is separated from the cathode compartment by a cation selective membrane, an aqueous suspension of potassium acid terephthalate at a molar concentration of from about 0.2 to about 1.0 and containing a potassium salt of an acid having a $pK_a$ greater than 4.8 to form an aqueous suspension of terephthalic acid and separating said terephthalic acid product, said electrolysis being conducted at a temperature of from about 20° to about 120° C, at a pH of from about 3 to about 4, a current density of from about 100 to about 500 amps per square foot, and at a voltage of from about 5 to about 12 volts.

2. The process of claim 1 wherein the anode of said cell is electroplated platinum.

3. The process of claim 2 wherein the cell is operated at a temperature between about 80° and about 95° C, a current density of from about 400 to about 450 ASF and a voltage of about 5 to about 6.5 volts.

4. The process of claim 3 where the cation selective membrane is a perfluorosulfonic acid resin.

5. A process for the preparation of terephthalic acid which comprises hydrolyzing terephthalonitrile in an aqueous medium containing dipotassium terephthalate, potassium bicarbonate and potassium hydroxide at a temperature of between about 100° and about 250° C, stripping ammonia and $CO_2$ from the aqueous medium, adding $CO_2$ to the stripped aqueous solution to precipitate potassium acid terephthalate, repulping said separated potassium acid terephthalate to obtain an aqueous suspension of from about 0.2 to about 1.0 moles per liter of potassium acid terephthalate and subjecting said suspension containing a potassium salt of an acid having a $pK_a$ above 4.8 to electrolysis in the anode compartment of an electrolysis cell wherein said anode compartment is separated from the cathode compartment by a cation selective membrane to form an aqueous suspension of terephthalic acid and separating said terephthalic acid product, said electrolysis being conducted at a temperature of from about 20° to about 120° C, at a pH of from about 3 to about 4, a current density of from about 100 to about 500 amps per square foot, and at a voltage of from about 5 to about 12 volts.

6. The process of claim 5 where the cation selective membrane is a perfluorinated sulfonic or carboxylic acid resin and the anode is electroplated platinum.

7. The process of claim 6 where the cell is operated at a temperature between about 80° and about 95° C, a current density of from about 400 to about 450 ASF, voltage of from about 5 to about 6.5 volts and the concentration of potassium acid terephthalate in the anode compartment is from about 0.25 to about 0.5 moles per liter.

* * * * *